United States Patent [19]

Pearce

[11] Patent Number: 5,318,993
[45] Date of Patent: Jun. 7, 1994

[54] ANTIHYPERLIPIDEMIC BENZOQUINONES

[75] Inventor: Bradley C. Pearce, East Hampton, Conn.

[73] Assignee: Bristol-Myers Squibb Company, New York, N.Y.

[21] Appl. No.: 48,695

[22] Filed: Apr. 16, 1993

[51] Int. Cl.⁵ .............................................. A61K 31/12
[52] U.S. Cl. ...................................... 514/690; 560/132; 552/293; 552/307; 552/308; 552/309; 552/310; 514/519
[58] Field of Search ............... 552/293, 307, 308, 309, 552/310; 560/132; 514/690, 519

[56] References Cited

U.S. PATENT DOCUMENTS

| | | | |
|---|---|---|---|
| 4,533,554 | 8/1985 | Terao et al. | 552/307 |
| 4,559,177 | 12/1985 | Dkutani et al. | 552/307 |
| 4,874,752 | 10/1989 | Terao et al. | 552/307 |
| 5,180,742 | 1/1993 | Terao et al. | 552/307 |

OTHER PUBLICATIONS

Sato et al., J. of Natural Products, vol. 52, pp. 975–981 (1989).
Sato et al., Chem. Abst., vol. 109, #110, 257r (1988).
Sato et al., Chem. Abst., vol. 110, #193, 145x (1989).
Brown, et al, J. Lipid Res., 21:505–517 (1980).
Wright, et al, A Symposium On Drugs Affecting Lipid Metabolism, Houston, TX (Nov. 1989).
Boehme, H., et al, Z. Naturforsch, 26:341–352 (1971).
Forsmark, P., et al, FEBS Letters, 285:39–43 (1991).
Stocker, et al, Proc. Natl. Acad. Sci. U.S.A., 88:1646–1650 (1991).
Packer, et al, Res. Comm. Chem. Path & Pharm., 72:231–241 (1991).
Littarru, et al, Drugs Exptl. Clin. Res., 8:529–532 (1985).

Primary Examiner—James H. Reamer
Attorney, Agent, or Firm—Prabodh I. Almaula

[57] ABSTRACT

The present invention relates to novel benzoquinones which are useful as antihyperlipidemic agents. The present invention also provides a process for their preparation, pharmaceutical compositions, and a method for treating birds and mammals in need thereof which comprises administering to said host an effective amount of a benzoquinone of the present invention.

11 Claims, No Drawings

ANTIHYPERLIPIDEMIC BENZOQUINONES

BACKGROUND OF THE INVENTION

1. Field of the Invention

The present invention relates to benzoquinones, their use as antihyperlipidemic agents, a process for their preparation, and pharmaceutical compositions.

2. Description of the Art

It is generally recognized that high blood cholesterol levels are a significant risk factors in cardiovascular disease.

It has been established that 3-hydroxy-3-methylglutaryl coenzyme A reductase (HMGR) is the first rate limiting enzyme in the biosynthetic pathway for cholesterol, that inhibition of HMGR activity results in a decrease in serum total cholesterol and low density lipoprotein (LDL) cholesterol levels, and that a decrease in serum LDL-cholesterol levels is reflected in a reduction of plasma level of apolipoprotein B. (Brown, et al, *J. Lipid Res.* 21: 505-517 (1980)).

Tocotrienols have been shown to suppress HMGR resulting in the inhibition of cholesterol biosynthesis and a subsequent drop in LDL cholesterol, apolipoprotein B, thromboxane $B_2$, platelet factor 4 and glucose levels. (Wright, et al. *A Symposium On Drugs Affecting Lipid Metabolism,* Houston, Tex. (November 1989)).

Idebenone (Formula I) is marketed in Japan (Takeda-AVAN 1986) for age-related cerebrovascular disorders of the brain.

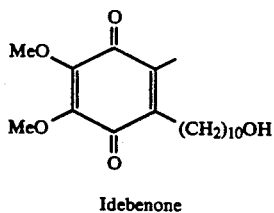

Idebenone

Pharmacokinetic studies with Idebenone in man have shown that the drug is absorbed rapidly and has somewhat poor (15-30%) bioavailability due to low intestinal absorption. Idebenone lacks the farnesylated side chain and would not be expected to exhibit hypocholesterolemic activity.

The ubiquinones, also known as Coenzymes Q, are a group of benzoquinones involved in electron transport mechanisms within mitochondria. The most common ubiquinone in mammalian systems is ubiquinone-10 (n=10, Formula II). The plastoquinones (Formula III) are found predominately in the chloroplasts of higher plants and play a similar role to the ubiquinones by acting as a redox carrier in the electron transport system. (Boehme, H., et al., *Z. Naturforsch.*, 26, 341-352 (1971)).

Vitamin $K_2$, also known as the menaquinones, are antihemorrahagic vitamins wherein n is ususally between 7-9 (Formula IV).

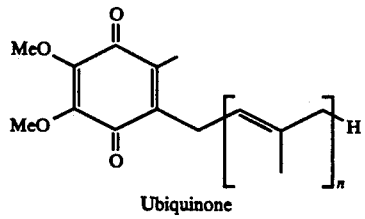

Ubiquinone

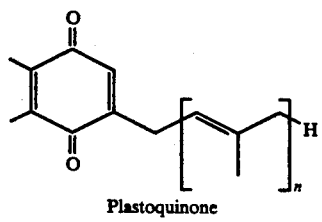

Plastoquinone

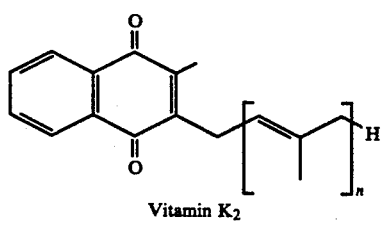

Vitamin $K_2$

Vitamin $K_2$ (n=4) was examined in vivo and appears to actually elevate cholesterol levels [Table II, intra].

Ubiquinol inhibits lipid peroxidation in submitochondrial particles. (Forsmark, P., et al. *FEBS Letters,* 285: 39-43 (1991)). Recently, Stocker et al. (Stocker, et al., *Proc. Natl. Acad. Sci. U.S.A.,* 88: 1646-1650, (1991)) have shown that ubiquinol-10 (the hydroquinone form of ubiquinone-10) is an inhibitor of LDL oxidation and is much more efficient than tocopherol in this respect. Packer et al. (Packer, et al., *Res. Comm. Chem. Path. & Pharm.,* 72: 231-241 (1991)) have shown that ubiquinone has a sparing effect on tocopherol in rat liver microsomes and mitochondrial membranes, Littarru et al. (Littarru, et al., *Drugs Exptl. Clin. Res.,* 8: 529-532 (1985)) have found that the ubiquinones are potent scavengers of superoxide. They indicated that preliminary evidence suggested that the reduced forms did not exhibit this activity.

SUMMARY OF THE INVENTION

The present invention provides benzoquinones which are useful as for cholesterol/lipid lowering in cases of hypercholesteremia, hyperlipidemia and atherosclerosis.

In one aspect, the present invention provides a pharmaceutical composition which comprises at least one compound of the present invention and a non-toxic pharmaceutically acceptable carrier.

Another aspect of the present invention provides a method of treating hypercholesteremia, hyperlipidemia and thromboembolic disorders in birds and mammals, including humans, which consists of administering at least one compound of the present invention to a host in need of such treatment.

Another aspect of the present invention provides intermediates useful in making the benzoquinones of Formula V infra.

These and other advantages and objects of the invention will be apparent to those skilled in the art.

DETAILED DESCRIPTION OF THE INVENTION

The present invention provides compounds of the general Formula V

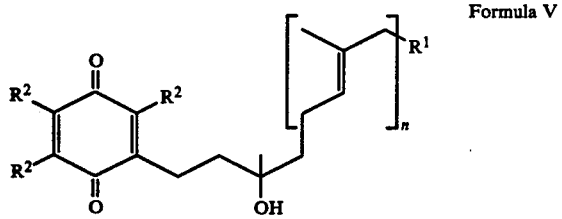

Formula V wherein
$R^1$ is H or

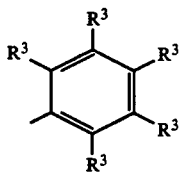

$R^2$ and $R^3$ are independently H, $C_1$-$C_5$ alkyl, $CF_3$, CN, halogen or $OCH_3$, and n is an integer of 1 to 3, or a pharmaceutical acceptable salt, hydrate or solvate thereof.

As used herein and in the claims (unless the context indicates otherwise) the term "$C_1$-$C_5$ alkyl" is meant to include branched or straight chain alkyl groups having 1 to 5 carbon atoms such as methyl, ethyl, propyl, isopropyl, butyl, isobutyl, t-butyl, and the like. The term "halogen" is meant to include fluorine, chlorine, bromine, iodine and the like.

Also included within the scope of the present invention are the pharmaceutically acceptable acid addition salts, the metal salts and the solvates of the compounds of Formula V which may exist in various tautomeric forms.

The quinones were prepared in good yields from the corresponding benzopyrans by oxidation with ceric ammonium nitrate.

Farnesyl benzoquinone (3) was prepared as shown in scheme I. Hydroquinone was di-acylated with diethylcarbamoyl chloride to give the nicely crystalline biscarbamate 1. Using the metalation procedure of Snieckus et al., (Snieckus, et al., *J. Org. Chem.*, 48: 1935-37 (1990)) carbamate 2 undergoes smooth lithiation with s-butyllithium. The lithio aromatic intermediate was alkylated with farnesyl bromide to give the farnesylated carbamate 2 in good yield. The carbamate was very resistant to hydrolytic cleavage, however farnesyl hydroquinone was cleanly obtained using lithium aluminum hydride. (Ochi, et al. *Chem. Lett.*, 831-32 (1979) and Cruz-Almanza, et al., *Synthetic Comm.*, 20: 1125-31 (1990)) Oxidation with ceric ammonium nitrate proceeds as described earlier to give the known farnesyl quinone, 3. (Ochi, et al., *Chem. Lett.*, 831-32 (1979)).

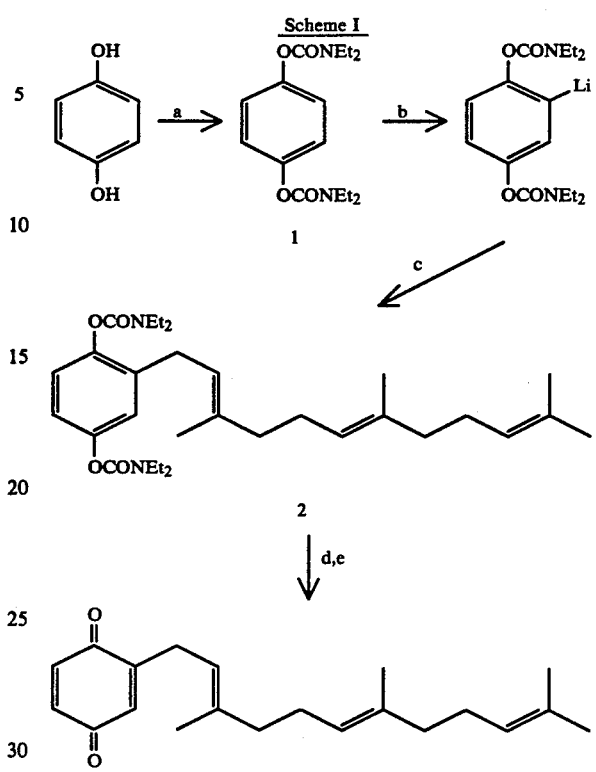

a) diethylcarbamoyl chloride ($ClCONEt_2$), sodium hydroxide, tetrahydrofuran;
b) s-Butyllithium, tetramethylethylenediamine, tetrahydrofuran, $-78°$ C.;
c) farnesyl bromide;
d) lithium aluminum hydride, tetrahydrofuran, Δ;
e) ceric ammonium nitrate, acetonitrile, water.

HEPG2 CELL CULTURE MODEL

The human hepatoma HepG2 cell culture model was employed to compare the intrinsic activities of the synthetic analogues relative to the tocotrienols. HepG2 cells were incubated with the indicated compounds for 4 hours at 10 μM. Cholesterol synthesis was assayed by $^{14}$C-acetate incorporation over the final hour of incubation, and HMG-CoA reductase suppression (specific activity) was assayed in the microsomal fraction isolated from parallel cultures at the end of the 4 hour incubation. Time course studies indicated that 4 hours preincubations provided maximal suppression of sterol synthesis. The results are shown in table I.

TABLE I

| Compound 10 μM | Percent of Control | |
|---|---|---|
| | Cholesterol Biosynthesis | HMGR Suppression |
| γ-Tocotrienol | 29 | 65 |
| Compound of Example 15 | 89 | 79 |
| Compound of Example 16 | 74 | N.T. |
| Compound of Example 14 | 10 | N.T. |
| Compound of Example 12 | 3 | 74 |
| Compound of Example 11 | 75 | N.T. |
| Compound of Example 13 | N.T. | N.T. |
| Compound of | | |

TABLE I-continued

| Compound 10 μM | Percent of Control | |
|---|---|---|
| | Cholesterol Biosynthesis | HMGR Suppression |
| Example 10 | 95 | N.T. |

IN VIVO EVALUATION OF SYNTHETIC ANALOGUES IN NORMOCHOLESTEROLEMIC CHICKENS

Hypocholesterolemic activity was evaluated for the synthetic analogues using γ-tocotrienol as a control in normocholesterolemic chickens. Newborn male chicks (6–10 for each group) were raised on a standard corn-soybean-based control diet for two weeks and then were switched to either control or experimental diets for four weeks. Drug treatment consisted of the addition of test compound to the corn-soybean-based. At the end of the feeding period, all the birds were fasted (about 36 hours) and refed (about 48 hours) to induce cholesterolgenic enzymes prior to sacrifice. The specific activity of HMG-CoA reductase, total serum cholesterol levels, HDL/LDL cholesterol pools, and triglyceride levels (data not shown) were examined (Table II).

TABLE II

Effects of BMS Compounds on Lipid Parameters in Male Chickens
Orally dosed for 4-weeks at 4 mg/kg/day

| Compound | Values Given as % of Control | | | |
|---|---|---|---|---|
| | Tot.-C | LDL-C | HDL-C | HMGR |
| γ-Tocotrienol | 76.3 | 54.8 | 87.0 | N.T. |
| Vitamin K$_2$ | 115.6 | 146.3 | 104.8 | N.T. |
| Example 15 | 76.7 | 59.0 | 90.5 | 67.4 |
| Example 16 | 93.8 | 94.9 | 95.8 | N.T. |
| Example 12 | 82.7 | 73.0 | 95.0 | N.T. |
| Example 11 | 87.2 | 80.1 | 96.9 | N.T. |
| Example 14 | 82.4 | 69.4 | 94.7 | N.T. |
| Example 13 | 57.7 | 32.0 | 75.6 | 59.9 |

N.T. = Not Tested

The compound of Example 15 is the quinone form of γ-tocotrienol and exhibits very similar cholesterol/HMGR suppression in vitro and in vivo [Tables I, II].

The compound of Example 15 is also very active in the cholesterol suppression assay in vitro and exhibits comparable activity to γ-tocotrienol in the chick model.

The results to the above tests demonstrates that the compounds of Formula V inhibit HMGR activity which results in a decrease in serum total cholesterol, and a decrease in LDL cholesterol levels.

Thus, the compounds of Formula V may be readily administered, to treat hypercholesterolemia, hyperlipidemia, and atherosclerosis in avian and mammalian systems in need of such treatment. For this purpose, the drug may be administered by conventional routes including, but not limited to, the alimentary canal in the form of oral doses, by injection in sterile parenteral preparations on nasally.

In yet another aspect, the present invention provides a pharmaceutical composition which comprises a compound of Formula V and a non-toxic pharmaceutically acceptable carrier. These carriers can be solid or liquid such as cornstarch, lactose, sucrose, olive oil or sesame oil. If a solid carrier is used, the dosage forms may be tablets, capsules, powders, troches or lozenges. If the liquid form is used, soft gelatin capsules, syrup or liquid suspensions, emulsions, or solutions in convenient dosage forms may be used. The composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiologically saline or some other sterile injectable medium immediately before use.

The dosage ranges will commonly range from about 50 mg to about 200 mg. Optimal dosages and regimes for a given host can be readily ascertained by those skilled in the art. It will, of course, be appreciated that the actual dose used will vary according to the particular composition formulated, the particular compound used, the disease being treated. Many factors that modify the action of the drug will be taken into account including age, weight, sex, diet, time of administration, route of administration, rate of excretion, condition of the patient, drug combinations, reaction sensitivities and severity of the disease.

All publications cited in this specification are indicative of the level of skill of those skilled in the art to which this invention pertains. Each publication is individually incorporated herein by reference in the location where it is cited.

The following examples are intended for illustrative purpose only and are not to be construed as limiting the invention in sphere or scope.

Melting points were recorded on a Thomas-Hoover melting point apparatus and are uncorrected. Boiling points are uncorrected. Infrared spectra were obtained on a Perkin-Elmer Model 1800 FT-IR spectrophotometer. $^1$H-NMR spectra were recorded on a Bruker AM 300 spectrometer or a Varian Gemini 300 NMR spectrometer; nuclear magnetic resonance (NMR) spectral characteristics refer to chemical shifts (δ) expressed in parts per million (ppm) with tetramethylsilane (TMS) as an internal standard. The relative area reported for the various shifts in the proton NMR spectral data corresponds to the number of hydrogen atoms of a particular functional type in the molecule. Mass spectra were measured on a Finnegan 4500 spectrometer (low resolution).

Thin-layer chromatography was performed on silica gel 60 F-254 plates purchased from E. Merck and company (visualization with iodine or phosphomolybdic acid); flash chromatography was performed on fine silica (EM Sciences, 230–240 mesh). All reactions were run under dry nitrogen unless otherwise indicated. Dry solvents were purchased from Aldrich, Milwaukee, Wis. in sure/seal bottles and transferred by syringe under nitrogen. Most commercially available starting materials did not require further purification.

EXAMPLE 1

1,4-Hydroquinone Bis-diethylcarbamate, (1)

Hydroquinone (10 g, 0.09 mole), diethylcarbamoyl chloride (23.5 mL, 0.2 mole), and sodium hydride (50%, 10.04 g, 0.21 mole) Were added under nitrogen to 150 mL of dry THF. The mixture was carefully warmed to initiate the reaction, then was heated at reflux for about 2 hours. The solution was cooled to 23°, filtered through celite, and concentrated in vacuo to yield a solid material. The solid was triturated with hexanes to remove the oil from the sodium hydride. Recrystallization of the crude solid from cyclohexane yielded white needles (25.4 g, 0.082 mole, 92%), mp 103°–104°: IR (KBr) 2982, 1711, 1474, 1418, 1274, 1216, 1186, 1156 cm$^{-1}$; $^1$H NMR (CDCl$_3$) δ 1.92 (m, 12H), 3.37 (m, 8H), 7.07 (s, 4H); MS m/e 309 (MH+).

Anal. Calcd. for C$_{16}$H$_{24}$N$_2$O$_4$: C, 62.32; H, 7.85; N, 9.09. Found: C, 62.35; H, 7.84; N, 9.08.

EXAMPLE 2

2-(3,7,11-Trimethyl-2(E),6(E),10-dodecatrienyl)-1,4-Hydroquinone Bis-diethylcarbamate, (2)

1,4-Hydroquinone bis-diethylcarbamate (4.42 g, 14.3 mmole), and tetramethylethylenediamine (TMEDA) (2.26 mL, 15 mmole) were dissolved in 100 mL of THF. The mixture was cooled to about −78° under nitrogen. s-Butyllithium (1.3M, 11.6 mL, 14.3 mmole) was added dropwise, and the solution was stirred for about 1 hour. Freshly prepared farnesyl bromide (4.3 g, 15.09 mmole) was added to the metalated carbamate as a THF solution (10 mL). After stirring for about 1 hour at about −78° the mixture was quenched with 1N HCl, poured into water and extracted with ether. The organic extracts were dried (brine, MgSO$_4$) and concentrated in vacuo. Purification of the crude material by flash chromatography [gradient 9:1 to 3:1 Hexanes:Et$_2$O] yielded the title compound as a clear oil (5.33 g, 10.41 mmole, 73%): IR (Film) 2992, 1724, 1420, 1279, 1187, 1160 cm$^{-1}$; $^1$H NMR (CDCl$_3$) δ 1.20 (m, 12H), 1.56 (s, 9H), 1.95–2.05 (m, 8H), 3.24 (d, J=6.8 Hz, 2H), 3.37 (m, 5H), 5.09 (m, 2H), 5.26 (t, J=6.8 Hz, 1H), 6.9–7.07 (m, 3H); MS m/e 513 (MH+).

Anal. Calcd. for C$_{31}$H$_{46}$N$_2$O$_4$: C, 72.62; H, 9.44; N, 5.46. Found: C, 72.57; H, 9.52; N, 5.64.

EXAMPLE 3

2,3-Dihydro-6-hydroxy-2-(4,8,12-trimethyltrideca-3(E),7(E),11-trienyl)-4H-1-benzopyran-4-one A mixture of 2,5-dihydroxyacetophenone [Aldrich Chemical], farnesyl acetaldehyde (Coates, et al., *J. Org. Chem.*, 43: 4915–4922 (1978))(30 mmol), and pyrrolidine (90 mmol) were dissolved in 30 mL of absolute ethanol under N$_2$. Powdered 3A° molecular sieves (5 g) was added to the mixture. The mixture was stirred at about 23° C. for about 24 hours. The reaction mixture was poured into 1N HCl, and extracted with ether. The organic extracts were dried (brine, MgSO$_4$), and concentrated in vacuo to a thick oil. The title compound was purified by flash chromatography. Yellow oil [Kugelrohr oven (bath 200–210° C./0.05 mm)]: IR (KBr) 3372, 2918, 1674, 1620, 1494, 1462, 1258, 1220, 828 cm$^{-1}$; $^1$H NMR (CDCl$_3$) δ 1.56 (s, 3H), 1.58 (s, 3H), 1.62 (s, 3H), 1.66 (s, 3H), 1.70 (m, 2H), 1.89–2.05 (m, 8H), 2.22 (m, 2H), 2.64 (s, 1H), 2.66 (d, J=2.8 Hz, 1H), 4.37 (m, 1H), 5.04–5.14 (m, 3H), 5.37 (br s, 1H), 6.88 (d, J=8.9 Hz, 1H), 7.04 (dd, J=3.2, 8.9 Hz, 1H), 7.33 (d, J=3.2 Hz, 1H); MS m/e 383 (MH+).

Anal. Calcd. (C$_{25}$H$_{34}$O$_3$): C, 78.49; H, 8.96; Found: C, 78.26, H, 9.00.

EXAMPLE 4

3,4-Dihydro-2-(4,8,12-trimethyltrideca-3(E),7(E),11-trienyl)-2H-1-benzopyran-6-ol 2,3-Dihydro-6-hydroxy-2-(4,8,12-trimethyltrideca-3(E),7(E),11-trienyl)-4H-1-benzopyran-4-one (3 mmol) was silylated with tert-butyldimethylsilyl chloride (3.3 mmol), and imidazole (3.6 mmol) in DMF (5 mL) for about 18 hours at about 23° C. The mixture was poured into water and extracted into ether. The ether solutions were dried (brine, MgSO$_4$), and concentrated in vacuo. The crude silylated tocotrienol was purified by flash chromatography. The reduction process was carried out using lithium aluminum hydride (1 equiv.) in ether at about −78° C. The crude alcohols (3 mmol) were added to lithium (9 mmol) dissolved in a 1:1 mixture of liquid ammonia:THF (24 mL) at about −78° C. Solid powdered ammonium chloride (3 g) was added to the mixture. The reaction was complete within 2 hours. Evaporation of the ammonia gave the crude silylated tocotrienol. The silylated tocotrienol was then deprotected (n-Bu$_4$NF) and purified by flash chromatography. Colorless oil [Kugelrohr oven (bath 160° C./0.03 mm)]: IR (KBr) 3388, 2924, 1494, 1450, 1218, 1052 cm$^{-1}$; $^1$H NMR (CDCl$_3$) δ 1.58 (s, 6H), 1.64 (s, 3H), 1.68 (s, 3H), 1.73 (m, 2H), 1.88–2.10 (m, 10H), 2.19 (m, 2H), 2.63–2.85 (m, 2H), 3.89 (m, 1H), 4.30 (br s, 1H), 5.08 (m, 2H), 5.15 (t, J=7.9 Hz, 1H), 6.52–6.58 (m, 2H), 6.67 (d, J=8.6 Hz, 1H); MS m/e 369 (MH+).

Anal. Calcd. (C$_{25}$H$_{36}$O$_2$): C, 81.47; H, 9.85; Found: C, 81.19; H, 9.86.

EXAMPLE 5

2,3-Dihydro-7,8-dimethyl-6-hydroxy-2-(4,8,12-trimethyltrideca-3(E),7(E),11-trienyl)-4H-1-benzopyran-4-one A mixture of 3,4-dimethyl-2,5-dihydroxyacetophenone (Manecke, et al., *Chem. Ber.* 95, 1413–16 (1962)) (30 mmol), farnesyl acetaldehyde (Coates, et al., *J. Org. Chem.* 43: 4915–4922 (1978)) (30 mmol), and pyrrolidine (90 mmol) were dissolved in 30 mL of absolute ethanol under N$_2$. Powdered 3A° molecular sieves (5 g) was added to the mixture. The mixture was stirred at about 23° C. for about 24 hours. The reaction mixture was poured into 1N HCl, and extracted with ether. The organic extracts were dried (brine, MgSO$_4$), and concentrated in vacuo to a thick oil. The 4-oxo-tocotrienol was purified by flash chromatography, and was recrystallized from hexanes. Yellow solid, mp 60°–62.5° C.: IR (KBr) 3292, 2922, 1664, 1606, 1440, 1230, 1090 cm$^{-1}$; $^1$H NMR (CDCl$_3$) δ 1.56 (s, 3H), 1.57 (s, 3H), 1.61 (s, 3H), 1.66 (s, 3H), 1.70 (m, 2H), 1.89–2.05 (m, 8H), 2.17 (s, 3H), 2.21 (s, 3H), 2.22 (m, 2H), 2.59 (s, 1H), 2.61 (d, J=4.1 Hz, 1H), 4.32 (m, 1H), 5.06 (m, 2H), 5.14 (t, J=7.1 Hz, 1H), 5.33 (br s, 1H), 7.18 (s, 1 H); MS m/e 411 (MH+).

Anal. Calcd. (C$_{27}$H$_{38}$O$_3$): C, 78.98; H, 9.33; Found: C, 79.40; H, 9.35.

EXAMPLE 6

3,4-Dihydro-7,8-dimethyl-2-(4,8,12-trimethyltrideca-3(E),7(E),11-trienyl)-2H-1-benzopyran-6-ol 2,3-Dihydro-7,8-dimethyl-6-hydroxy-2-(4,8,12-trimethyltrideca-3(E),7(E),11-trienyl)-4H-1-benzopyran-4-one (3 mmol) was silylated with tert-butyldimethylsilyl chloride (3.3 mmol), and imidazole (3.6 mmol) in DMF (5 mL) for about 18 hours at about 23° C. The mixture was poured into water and extracted into ether. The ether solutions were dried (brine, MgSO$_4$), and concentrated in vacuo. The crude silylated tocotrienol was purified by flash chromatography. The reduction process is carried out using lithium aluminum hydride (1 equiv.) in ether at about −78° C. The crude alcohols (3 mmol) were added to lithium (9 mmol) dissolved in a 1:1 mixture of liquid ammonia:THF (24 mL) at about −78° C. Solid powdered ammonium chloride (3 g) was added to the mixture. The reaction was complete within 2 hours. Evaporation of the ammonia gave the crude silylated tocotrienol. The silylated tocotrienol was then deprotected (n-Bu$_4$NF) and purified by flash chromatography. White needles (hexanes), mp 70°-71° C.: IR (KBr) 3312, 2926, 1622, 1502, 1446, 1232, 1080 cm$^{-1}$; $^1$H NMR (CDCl$_3$) δ 1.59 (s, 6H), 1.63 (s, 3H), 1.68 (s, 3H), 1.73 (m, 2H), 1.88-2.10 (m, 10H), 2.13 (s, 6H), 2.22 (m, 2H), 2.60-2.85 (m, 2H), 3.87 (m, 1H), 4.21 (s, 1H), 5.07 (m, 2H), 5.18 (t, J=7.1 Hz, 1H), 6.35 (s, 1H); MS m/e 397 (MH+).

Anal. Calcd. (C$_{27}$H$_{40}$O$_2$): C, 81.77; H, 10.17; Found: C, 81.93; H, 10.18.

EXAMPLE 7

3,4-Dihydro-2,7,8-Trimethyl-2-[4-Methyl-6-[3-(Trifluoro-methyl)phenyl-3-hexenyl-2H-1-Benzopyran-6-ol 2,3-Dihydro-6-Hydroxy-2,7,8-Trimethyl-2-(4-Methylpent-3-enyl)-4H-1-Benzopyran-4-One 2,5-Dihydroxy-3,4-dimethylacetophenone (50 g, 0.28 mole), 6-methyl-5-hepten-2-one (70 g, 0.55 mole), 4A° molecular sieves (15 g, powdered), and pyrrolidine (60 g, 0.84 mole) were combined in 250 mL of absolute ethanol. The mixture was stirred under nitrogen at reflux temperature for a period of 15 hours. The dark solution was cooled, poured into 1N HCl and extracted into ether. The ether layers were washed with water, dried (brine, MgSO$_4$), filtered to remove the sieves and concentrated in vacuo to give a dark brown solid. The product was purified by recrystallization from acetonitrile (×2) to yield the title compound as a beige solid (37.3 g, 0.13 mole, 46% yield). An analytical sample was prepared by one more recrystallization from acetonitrile to give a yellow solid mp 143°: IR (KBr) 3436, 2968, 1670, 1608, 1460, 1242 cm$^{-1}$; $^1$H NMR (CDCl$_3$) δ 1.38 (s, 3H), 1.56 (s, 3H), 1.62 (m, 1H), 1.58 (s, 3H), 1.81 (m, 1H), 2.10 (m, 2H), 2.15 (s, 3H), 2.22 (s, 3H), 2.55,2.73 (ABq, J=16.6Hz, 2H), 5.06 (t, J=5.7 Hz), 5.93 (s,1H), 7.27 (s,1H); MS m/e 289 (MH+).

Anal. Calcd. for C$_{18}$H$_{24}$O$_3$: C, 74.97; H, 8.39. Found: C, 74.73; H, 8.28.

2,3-Dihydro-6-[(1,1-Dimethylethyl)dimethylsilyloxy]-2,7,8-Trimethyl-2-(4-Methylpent-3-enyl)-4H-1-Benzopyran-4-One A mixture of 2,3-dihydro-6-hydroxy-2,7,8-trimethyl-2-(4-methylpent-3-enyl)-4H-1-benzopyran-4-one (9.4 q, 34.3 mmole), tert-butyldimethylsilyl chloride (7.75 g, 51.5 mmole), and imidazole (6.99 g, 0.1 mole) were dissolved in 50 mL of dry DMF. The solution was stirred under nitrogen for about 18 hours, poured into water and extracted with ether. The organic layers were dried (brine, MgSO$_4$) and concentrated in vacuo. The crude material was purified by flash chromatography (gradient 20:1 to 10:1 hexanes:ether) to give the title compound as a colorless oil (9.9 g, 24.6 mmole, 72%): $^1$H NMR (CDCl$_3$) δ 0.20 (s, 6H), 1.0 (s, 9H), 1.37 (s, 3H), 1.55 (s, 3H), 1.55-1.60 (m, 1H), 1.65 (s, 3H), 1.74-1.84 (m, 1H), 2.0-2.1 (m, 2H), 2.14 (s, 3H), 2.16 (s, 3H), 2.63 (ABq, J=16.5 Hz, 2H), 5.07 (t, J=7.0 Hz, 1H), 7.09 (s, 1H); MS m/e 403 (MH+).

2,3-Dihydro-6-[(1,1-Dimethylethyl)dimethylsilyloxy]-2,7,8-Trimethyl-2-(4-Methyl-3-Pentenyl)-2H-1-Benzopyran Aluminum chloride (42.4 g, 0.318 mole) was dissolved in 300 mL of dry ether cooled to 0° under nitrogen. Lithium aluminum hydride (6.04 g, 0.159 mole) was added, and the resulting slurry was stirred at about 0° for about 1 hour. 2,3-Dihydro-6-[(1,1-dimethylethyl)-dimethylsilyloxy]-2,7,8-trimethyl-2-(4-methylpent-3-enyl)-4H-1-benzopyran-4-one (32 g, 0.08 mole) was added as an ether solution (150 mL) dropwise over a period of 0.5 hours. After about 0.5 hour at about −5°, TLC (3:1 Hex.: Et$_2$O) indicated complete reduction, and the mixture was quenched by the slow addition of saturated Na$_2$SO$_4$ solution. The mixture was poured into 1N HCl and extracted with ether. The combined organic fractions were washed with water, extracted into fresh ether and dried (brine, MgSO$_4$). Concentration in vacuo gave a colorless oil that was purified by flash chromatography (gradient 20:1 to 10:1 hexanes:ether).to give the title compound as a colorless oil (29 g, 0.075 mole, 93% yield): IR (film) 2930, 2858, 1472, 1426, 252, 1230, 1094 cm$^{-1}$; $^1$H NMR (CDCl$_3$) δ 0.16 (s, 6H), 0.98 (s, 9H), 1.24 (s, 3H), 1.47-1.85 (m, 4H), 1.58 (s, 3H), 1.66 (s, 3H), 2.08 (s, 3H), 2.10 (m, 2H), 2.66 (t, J=6.2 Hz, 2H), 5.11 (t, J=5.8Hz), 6.33 (s,1H); MS m/e 389 (MH+).

Anal. Calcd. for C$_{24}$H$_{40}$O$_2$Si$_1$: C, 74.17; H, 10.37. Found: C, 74.21; H, 10.22.

[3,4-Dihydro-6-[(1,1-Dimethylethyl)dimethylsilyloxy]-2,7,8-Trimethyl-2H-1-Benzopyran-2-Yl]-3-Propanal 2,3-Dihydro-6-[(1,1-dimethylethyl) dimethylsilyloxy]-2,7,8-trimethyl-2-(4-methyl-3-pentenyl)-2H-1-benzopyran (29 g, 0.075 mole) was dissolved in 500 mL of CH$_2$Cl$_2$ containing 34 mL of MeOH. The solution was cooled to −78° while ozone/oxygen was bubbled through the mixture. The reaction was followed by TLC (2:1 Hex.: Et$_2$O) and when the less polar olefin was reduced to about 80%, the process was stopped. The mixture was warmed to about −5° and dimethyl sulfide (34 mL) was added. After stirring for about 12 hours at about 23°, the mixture tested negative for peroxide, and the volatile components were stripped off in vacuo leaving a yellow oil which was directly purified by flash chromatography (gradient 10:1 to 7:1 Hexanes-:Et$_2$O) to give the title compound, (18.4 g, 0.051 mmole, 68% yield) as a pale yellow oil: IR (film) 2954, 2930, 2858, 1726, 1472, 1426, 1252, 1228, 1094 cm$^{-1}$; $^1$H NMR (CDCl$_3$) δ 0.16 (s, 6H), 0.99 (s, 9H), 1.22 (s, 3H), 1.55-2.0 (m, 4H), 2.05 (s, 3H), 2.08 (s, 3H), 2.61 (t, J=7.7 Hz, 2H), 2.69 (m, 2H), 6.34 (s, 1H), 9.79 (t, J=1.6Hz, 1H); MS m/e 363 (MH+).

Anal. Calcd. for C$_{21}$H$_{34}$O$_3$Si$_1$: C, 69.57; H, 9.45. Found: C, 69.64; H, 9.46.

Ethyl 5-[3,4-Dihydro-6-[(1,1-Dimethylethyl)dimethylsilyloxy]-2,7,8-Trimethyl-2H-1-Benzopyran-2-Yl]-2(E)-Pentenoate

[3,4-Dihydro-6-[(1,1-dimethylethyl)dimethylsilyloxy]-2,7,8-trimethyl-2H-1-benzopyran-2-yl]-3-propanal (8.1 g, 22.4 mmole) and ethyl 2-(triphenylphosphoranylidene)propionate (9.7 g, 26.9 mmole) were dissolved, with cooling (0°, 30 min) in 200 mL of dry CH$_2$Cl$_2$. After about 18 hours at about 23°, TLC (4:1 Hexanes:Et$_2$O) indicated the reaction complete and the solvent was removed in vacuo. The oily yellow solid was triturated with 1:1 hexanes:ether, and the solid material was removed by filtration. The solvents were removed in vacuo to give a yellow oil which was purified by flash chromatography (gradient 20:1 to 7:1 hexanes:ether) to give the title compound (7.4 g, 16.6 mmole, 74%) as a pale yellow oil. A sample was distilled in a Kugelrohr oven (bath 190°-200°/0.1 mm) for analytical purposes: IR (film) 2940, 1710, 1475, 1425, 1260, 1095, 840 cm$^{-1}$; $^1$H NMR (CDCl$_3$) δ 0.16 (s, 6H), 1.00 (s, 9H), 1.25 (s, 3H), 1.27 (t, J=7.1 Hz, 3H), 1.56–1.80 (m, 4H), 1.81 (s, 3H), 2.08 (s, 6H), 2.32 (m, 2H), 2.68 (m, 2H), 4.16 (q, J=7.1 Hz, 2H), 6.34 (s, 1H), 6.76 (t, J=6.1 Hz, 1H); MS m/e 446 (M+).

Anal. Calcd. for C$_{26}$H$_{42}$O$_4$Si$_1$: C, 69.91; H, 9.48. Found: C, 70.20; H, 9.65.

[2-(5-Hydroxy-4-Methyl-3(E)-Pentenyl)]-3,4-Dihydro-6-[(1,1-Dimethylethyl)dimethylsilyloxy]-2,7,8-Trimethyl-2H-1-Benzopyran To a suspension of LiAlH$_4$ (3.32 g, 87.3 mmole) in 250 mL of dry ether cooled to about −5° was added AlCl$_3$ (3.87 g, 29.1 mmole) portionwise. After stirring the slurry of alane for about 0.5 hour at about −5°, ethyl 5-[3,4-dihydro-6-[(1,1-dimethylethyl) dimethylsilyloxy]-2,7,8-trimethyl-2H-1-benzopyran-2-yl]-2(e)-pentenoate (8.65 g, 19.4 mmole) was added as an ether solution (20 mL) dropwise over a period of 0.5 hour. After about 0.25 hour at about −5°, TLC (1:1 Hex.: Et$_2$O) indicated complete reduction of the ester and the mixture was quenched by the slow addition of saturated Na$_2$SO$_4$ solution. The aluminum salts were filtered and washed well with methanol. The combined organic fractions were washed with water, extracted into fresh ether and dried (Brine, MgSO$_4$) Concentration in vacuo gave a colorless oil (7.5 g) of crude material that was purified by flash chromatography (gradient 9:1 to 1:1 hexanes:ether) to give the title compound as a colorless oil (6.55 g, 16.2 mmole, 84%). A portion was distilled in a Kugelrohr oven (bath 180°-190°/0.1 mm) for analytical purposes: IR (film) 3330, 1480, 1430, 1255, 1095, 840 cm$^{-1}$; $^1$H NMR (CDCl$_3$) δ 0.16 (s, 6H), 1.00 (s, 9H), 1.25 (s, 3H), 1.5–1.85 (m, 4H), 1.65 (s, 3H), 2.08 (s, 6H), 2.17 (m, 2H), 2.66 (m, 2H), 3.97 (d, J=5.7 Hz, 2H), 5.41 (t, J=7.2 Hz, 1H), 6.34 (s, 1H); MS m/e 404 (M+).

Anal. Calcd. for C$_{24}$H$_{40}$O$_3$Si$_1$: C, 71.24; H, 9.96. Found: C, 71.33; H, 9.43.

[2-(5-Chloro-4-Methyl-3(E)-Pentenyl)]-3,4-Dihydro-6-[(1,1-Dimethylethyl)dimethylsilyloxy]-2,7,8-Trimethyl-2H-1-Benzopyran Dimethylsulfide (1.48 mL, 20.2 mmole) was added dropwise to a solution of N-chlorosuccinimide (2.59 g, 19.4 mmole) in 100 mL of dry CH$_2$Cl$_2$ cooled to about −5°. The white suspension was stirred for about 0.45 hour while [2-(5-hydroxy-4-methyl-3(E)-pentenyl)]-3,4-dihydro-6-[(1,1-dimethylethyl) dimethylsilyloxy]-2,7,8-trimethyl-2H-1-benzopyran (6.27 g, 15.52 mmole) was added as a CH$_2$Cl$_2$ solution (20 mL). The clear solution was stirred for about 2.0 hours at about −5° at which time TLC (2:1 Hex.: Et$_2$O) indicated complete conversion to a less polar spot. The CH$_2$Cl$_2$ was removed in vacuo (<40°) leaving an oily solid. The material was triturated with ether, filtered, and concentrated in vacuo (<40°) to a pale yellow oil. The oil was immediately flushed through a pad of silica gel (gradient 9:1 to 1:1 Hex.: Et$_2$O) to give the title chloride as a pale yellow oil (6.22 g, 14.72 mmole, 95%) that solidified on standing (mp 56°-58°): IR (film) 2940, 1480, 1430, 1255, 1095, 845 cm$^{-1}$; $^1$H NMR (CDCl$_3$) δ 0.16 (s, 6H), 1.00 (s, 9H), 1.24 (s, 3H), 1.50–1.80 (m, 4H), 1.68 (s, 3H), 2.08 (s, 6H), 2.18 (m, 2H), 2.67 (m, 2H), 3.99 (s, 2H), 5.54 (t, J=6.7 Hz, 1H), 6.34 (s, 1H); MS m/e 422 (M+).

Anal. Calcd. for C$_{24}$H$_{39}$Cl$_1$O$_2$Si$_1$: C, 68.13; H, 9.29. Found: C, 68.27; H, 9.36.

4-Methyl-1-[[[3-(Trifluoromethyl)phenyl]methyl]sulfonyl]benzene

3-Trifluoromethylbenzyl bromide (50 mmole) and sodium p-toluenesulfinate (65 mmole) were dissolved in 100 mL of dry DMF. The mixture was stirred at about 23° for about 18 hours then diluted with water. The sulfone crystallized from the aqueous mixture and was filtered. The compound was purified by recrystallization (EtOH). Colorless plates, mp 139°-140°: IR (KBr) 2954, 1614, 1598, 1450, 1332, 1312, 1288, 1164, 1142, 1116, 1074 cm$^{-1}$; $^1$H NMR (CDCl$_3$) δ 2.44 (s, 3H), 4.34 (s, 2H), 7.16 (s, 1H), 7.26 (d, J=8.1 Hz, 2H), 7.42 (m, 1H), 7.50 (d, J=8.1 Hz, 2H), 7.58 (d, J=7.5 Hz, 1H); MS m/e 315 (MH+).

Anal. Calcd. for C$_{15}$H$_{13}$F$_3$O$_2$S$_1$: C, 57.32; H, 4.17. Found: C, 57.28; H, 4.08.

3,4-Dihydro-6-[(1,1-Dimethylethyl)dimethylsilyloxy]-2-[4-Methyl-6-[(4-Methylphenyl)sulfonyl]-6-[3-(Trifluoromethyl)phenyl]-3-hexenyl]-2,7,8-Trimethyl-2H-1-Benzopyran 4-Methyl-1-[[[3-(trifluoromethyl)phenyl]methyl]sulfonyl]benzene (30 mmole) was dissolved in 100 mL of dry THF. The mixture was cooled to about −78° under nitrogen, and n-butyllithium (30 mmole) was added dropwise giving rise to a colored anion [yellowish-orange]. The solution was stirred for about 1 hour at about −78° before the addition of HMPA (5 mL) and [2-(5-chloro-4-methyl-3(E)-pentenyl)]-3,4-dihydro-6-[(1,1- dimethylethyl)dimethyl silyloxy]-2,7,8-trimethyl-2H-1-benzopyran (25 mmole). The mixture was stirred for about 1 hour at about −78°, then warmed to about −5° for about 12 hours, and poured into 1N HCl. The mixture was extracted with fresh ether. The combined organic fractions were washed With water and dried (brine, MgSO$_4$). Concentration in vacuo gave a crude material that was purified by flash chromatography (gradient 10:1 to 2:1 hexanes:ether) to give the coupled product as colorless oil: IR (film) 2930, 1472, 1450, 1424, 1330, 1166, 1146, 1130, 1088 cm$^{-1}$; $^1$H NMR (CDCl$_3$) δ 0.16 (s, 6H), 1.00 (s, 9H), 1.09, 1.10 (s, 3H), 1.28 (m, 2H), 1.41, 1.39 (s, 3H), 1.60 (m, 2H), 1.91 (m, 2H), 2.02 (s, 3H), 2.07 (s, 3H), 2.39 (s, 3H), 2.56 (m, 2H), 2.74 (t, J=13.9 Hz, 1H), 3.09 (d, J=11.9 Hz, 1H), 4.22 (d of t, J=12.1, 4.0 Hz, 1H), 5.06 (m, 1H), 6.30 (s, 1H), 7.10 (s, 1H), 7.18 (d, J=8.5 Hz, 2H), 7.36 (m, 4H), 7.48 (d, J=6.5 Hz, 1H); MS m/e 701 (MH+).

Anal. Calcd. for C$_{39}$H$_{51}$F$_3$O$_4$S$_1$Si$_1$: C, 66.83; H, 7.33. Found: C, 66.71; H, 7.18.

3,4-Dihydro-2,7,8-Trimethyl-2-[4-Methyl-6-[3-(Trifluoro-methyl)phenyl]-3-hexenyl]-2H-1-Benzopyran-6-ol 3,4-Dihydro-6-[(1,1-dimethylethyl) dimethylsilyloxy]-2-[4-methyl-6-[(4-methylphenyl)sulfonyl]-6-[3-(trifluoromethyl)phenyl]-3-hexenyl]-2,7,8-trimethyl-2H-1- benzopyran. (25 mmole) was dissolved in 100 mL of methanol. Pulverized sodium monohydrogen sulfate (0.1 mole) was added to the methanol solution. The mixture was cooled to about 0°, and sodium amalgam (40 g, 6% Na) was added to the suspension. The mixture was stirred for about 1 hour at about 0°, then warmed to about 23° for about 3 hours. Additional amalgam was added to the decanted [from mercury] solution for completion of the reaction before pouring into 1N HCl. The mixture was extracted with ether, and the combined organic fractions were washed with water and dried (brine, MgSO$_4$). Concentration in vacuo gave a crude material that was taken directly to the phenol. The silyl ether was treated with tetra-n-butylammonium floride (30 mmole) in ether (100 mL). The mixture was poured into 1N HCl and extracted with ether. The combined organic fractions were washed with water and dried (brine, MgSO$_4$). Concentration in vacuo gave a crude material that was purified by flash chromatography (gradient 10:1 to 2:1 hexanes:ether) to give the title compound as a light brown oil: IR (film) 3406, 2932, 1492, 1448, 1426, 1328, 1124, 1074 cm$^{-1}$; $^1$H NMR (CDCl$_3$) δ 1.24 (s, 3H), 1.40–1.70 (m, 4H), 1.64 (s, 3H), 2.10 (m, 2H), 2.11 (s, 3H), 2.13 (s, 3H), 2.24 (t, J=8.8Hz, 2H), 2.67 (m, 4H), 4.23 (s, 1H), 5.13 (t, J=7.1 Hz, 1H), 6.38 (s, 1H), 7.34–7.41 (m, 4H); MS m/e 433 (MH+).

Anal. Calcd. for C$_{26}$H$_{31}$F$_3$O$_2$: C, 72.20; H, 7.22. Found: C, 72.12; H, 7.28.

EXAMPLE 8

3,4-Dihydro-2-methyl-2-(4,8,12-trimethyl-3(E),7(E),11-tridecatrienyl)-2H-naphtho[1,2-b]-pyran-6-ol 2,3-Dihydro-6-hydroxy-2-methyl-2-(4,8,12-trimethyl-3(E),7(E),11-tridecatrienyl)-4H-naphtho[1,2-b]pyran-4-one A mixture of 1,4-dihydroxy-2-naphthophenone [Spruit, et al., *Rec. Trav. Chim.* 66: 655–672 (1947).], farnesylacetone [Isler, et al., *Helv. Chim. Acta.* 94: 786–807 (1958).] (30 mmol), and pyrrolidine (90 mmol) were dissolved in 30 mL of absolute ethanol under N$_2$. Powdered 3A° molecular sieves (5 g) was added to the mixture. The mixture was stirred at about 23° C. for about 24 hours. The reaction mixture was poured into 1N HCl, and extracted with ether. The organic extracts were dried (brine, MgSO$_4$), and concentrated in vacuo to a thick oil. The title compound was purified by flash chromatography. Yellow solid (pentane), mp 73°–74° C.: IR (KBr) 3280, 2920, 1670, 1655, 1440, 1420, 1175, 770 cm$^{-1}$; $^1$H NMR (CDCl$_3$) δ 1.51 (s, 3H), 1.56 (s, 3H), 1.58 (s, 6H), 1.66 (s, 3H), 1.78 (m, 2H), 1.90–2.10 (m, 8H), 2.20 (m, 2H), 2.74 and 2.89 (AB q, J=16.6Hz, 2H), 5.07 (m, 3H), 5.66 (s, 1H), 7.25 (s, 1H), 7.55 (t, J=6.9 Hz, 1H), 7.65 (t, J=6.9 Hz, 1H), 8.18 (d, J=8.4 Hz, 1H), 8.28 (d, J=8.4 Hz, 1 H); MS m/e 446 (M+).

Anal. Calcd. (C$_{30}$H$_{35}$O$_3$): C, 80.68; H, 8.58; Found: C, 80.39; H, 9.01.

2,3-Dihydro-6-hydroxy-2-methyl-2-(4,8,12-trimethyl-3(E),7(E) ,11-tridecatrienyl)-4H-naphtho[1,2-b]pyran-4-one (3 mmol) was silylated with tertbutyldimethylsilyl chloride (3.3 mmol), and imidazole (3.6 mmol) in DMF (5 mL) for about 18 hours at about 23° C. The mixture was poured into water and extracted into ether. The ether solutions were dried (brine, MgSO$_4$), and concentrated in vacuo. The crude silylated tocotrienol was purified by flash chromatography. The reduction process was carried out using lithium aluminum hydride (1 equiv.) in ether at about −78° C. The crude alcohols (3 mmol) were added to lithium (9 mmol) dissolved in a 1:1 mixture of liquid ammonia:THF (24 mL) at −78° C. Solid powdered ammonium chloride (3 g) was added to the mixture. The reaction was complete within 2 hours. Evaporation of the ammonia gave the crude silylated tocotrienol. The silylated tocotrienol was then deprotected (n-Bu$_4$NF) and purified by flash chromatography. Brown oil: IR (film) 3400, 2940, 1610, 1445, 1408, 1320, 1070, 775 cm$^{-1}$; $^1$H NMR (CDCl$_3$) δ 1.35 (s, 3H), 1.58 (s, 3H), 1.59 (s, 6H), 1.65–1.90 (m, 4H), 1.66 (s, 3H), 1.90–2.10 (m, 8H), 2.21 (m, 2H), 2.77 (m, 2H), 4.86 (s, 1H), 5.08 (m, 2H), 5.15 (m, 1H), 6.50 (br s, 1H), 7.45 (m, 2H), 8.04 (m, 1H), 8.16 (m, 1H); MS m/e 432 (M+).

Anal. Calcd. (C$_{30}$H$_{40}$O$_2$): C, 83.29; H, 9.32; Found: C, 83.52; H, 9.46.

EXAMPLE 9

General Procedure for Benzopyran Oxidation

The benzopyran (2.5 mmole) was dissolved in 50 mL of acetonitrile, and the mixture was cooled to about 10°. Ceric ammonium nitrate (3 mmole) dissolved in 7 mL of water was added dropwise to the acetonitrile solution. The mixture was stirred at 5–10° for about 15 minutes at which time TLC indicated the reaction to be complete. The mixture was poured into water and extracted with ether. The ether extracts were dried (brine, MgSO$_4$) and concentrated in vacuo. The crude quinones were purified by flash chromatography.

EXAMPLE 10

2-(3,7,11-Trimethyl-2(E),6(E),10-Dodecatrienyl)-2,5-Cyclohexadiene-4-Dione (3)

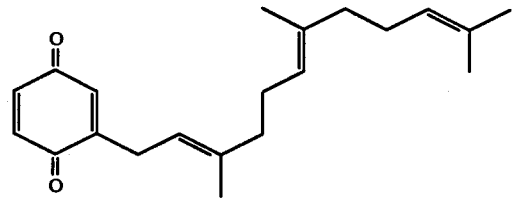

2-(3,7,11-Trimethyl-2(E),6(E),10-dodecatrienyl)-1,4-hydroquinone bis-diethylcarbamate 2 (1.62 g, 3.16 mmole) was dissolved in 30 mL of THF. Lithium aluminum hydride (240 mg, 6.33 mmole) was added and the mixture was heated to reflux under nitrogen for about 1.5 hours. TLC analysis indicated a small amount of starting material. An additional amount of LAH (50 mg) was added and the mixture was heated to reflux for about 1 hour. TLC analysis indicated a complete reaction. The mixture was quenched with 1N HCl, poured into water and extracted with ether. The organic extracts were dried (brine, MgSO$_4$) and concentrated in vacuo. Purification of the crude material by flash chromatography [gradient 6:1 to 3:1 Hexanes:Eth$_2$O] yielded 2-(3,7,11-trimethyl-2(E),6(E),10-dodecatrienyl)-1,4-hydroquinone as a clear oil (675 mg, 2.15 mmole, 56%): $^1$H NMR (CDCl$_3$) δ 1.57 (s, 6H), 1.65 (s, 3H), 1.74 (s, 3H), 1.90–2.15 (m, 8H), 3.25 (d, J=6.8Hz, 2H), 4.48 (s, 1H), 4.75 (s, 1H), 5.07 (m, 2H), 5.26 (t, J=6.8Hz, 1H), 6.58 (m, 2H), 6.65 (d, J=7.0 Hz, 1H).

The hydroquinone was oxidized with ceric ammonium nitrate as described in the general procedure to give the title compound as an orange oil: IR (film) 2918, 1658, 1600, 1448, 1298 cm$^{-1}$; $^1$H NMR (CDCl$_3$) δ 1.59 (s, 6H), 1.62 (s, 3H), 1.67 (s, 3H), 1.9–2.10 (m, 10H), 3.12

(d, J=7.3 2H), 5.12 (m, 3H), 6.52 (s, 1H), 6.67–6.77 (m, 2H); MS m/e 313 (MH+).

Anal. Calcd. for $C_{21}H_{28}O_2 \cdot 0.11\ H_2O$: C, 80.22; H, 9.05; 0.63% $H_2O$. Found: C, 80.22; H, 9.09; 1.74% $H_2O$.

EXAMPLE 11

2-(3-Hydroxy-7,11,15-Trimethyl-6(E),10(E),14-Hexadecatrienyl)-2,5-Cyclohexadiene-1,4-Dione

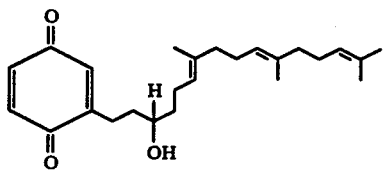

Reddish-Brown Oil: IR (film) 3450, 2924, 1658, 1600, 1446, 1382, 1292 cm$^{-1}$; $^1$H NMR (CDCl$_3$) δ 1.52 (m, 2H), 1.59 (s, 6H), 1.62 (s, 3H), 1.67 (s, 3H), 1.9–2.15 (m, 12H), 2.57 (m, 2H), 3.61 (m, 1H), 5.11 (m, 3H), 6.59 (s, 1H), 6.69–6.78 (m, 2H); MS m/e 385 (MH+).

Anal. Calcd. for $C_{25}H_{36}O_3$: C, 78.08; H, 9.44. Found: C, 78.22; H, 9.45.

EXAMPLE 12

5-(3-Hydroxy-7,11,15-Trimethyl-6(E),10(E),14-Hexadecatrienyl)-2,3-Dimethyl-2,5-Cyclohexadiene-1,4-Dione

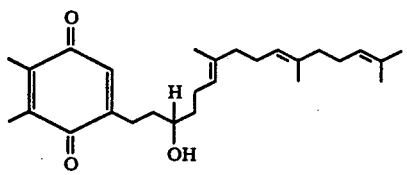

Yellow-Brown Oil: IR {film} 3442, 2924, 1648, 1616, 1446, 1378, 1318, 1104 cm$^{-1}$; $^1$H NMR (CDCl$_3$) δ 1.50 (m, 2H), 1.57 (s, 6H), 1.60 (s, 3H), 1.63 (s, 5H), 1.9–2.10 (m, 12H), 1.99 (s, 3H), 2.01 (s, 3H), 2.52 (m, 2H), 3.58 (m, 1H), 5.09 (m, 3H), 6.52 (s, 1H); MS m/e 413 (MH+).

Anal. Calcd. for $C_{27}H_{40}O_3$: C, 78.59; H, 9.77. Found: C, 78.87; H, 9.88.

EXAMPLE 13

5-(3,7-Dimethyl-3-Hydroxy-9-[3-(Trifluoromethyl)-phenyl]-6(E)-Nonenyl)-2,3-Dimethyl-2,5-cyclohexadiene-1,4-Dione

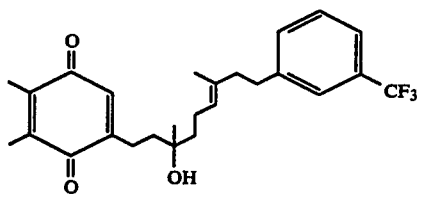

Reddish-Brown Oil: IR (film) 3518, 2930, 1648, 1616, 1450, 1378, 1328, 1124, 1074 cm$^{-1}$; $^1$H NMR (CDCl$_3$) δ 1.24 (s, 3H), 1.46 (m, 2H), 1.58 (m, 2H), 1.67 (s, 3H), 1.99 (s, 3H), 2.01 (s, 3H), 2.05 (m, 2H), 2.27 (t, J=7.2 Hz, 2H), 2.47 (m, 2H), 2.74 (m, 2H), 5.10 (m, 1H), 6.52 (s, 1H), 7.31–7.43 (m, 4H); MS m/e 449 (MH+).

Anal. Calcd. for $C_{26}H_{31}O_3$: C, 69.63; H, 6.97. Found: C, 69.79; H, 7.16.

EXAMPLE 14

2-(3-Hydroxy-3,7,11,15-Tetramethyl-6(E),10(E),14-Hexadecatrienyl)-1,4-Naphthalene-1,4-dione

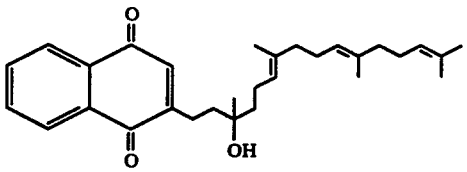

Orange Brown Oil: IR (film) 3510, 2924, 1662, 1596, 1448, 1302, 1264, 1110 cm$^{-1}$; $^1$H NMR (CDCl$_3$) δ 1.27 (s, 3H), 1.50–1.70 (m, 2H), 1.57 (s, 6H), 1.63 (s, 3H), 1.67 (s, 3H), 1.9–2.15 (m, 12H), 2.64 (m, 2H), 5.11 (m, 3H), 6.81 (s, 1H), 7.12 (m, 2H), 8.07 (m, 2H); MS [FAB] m/e 471 (M+Na+).

Anal. Calcd. for $C_{30}H_{40}O_3$: C, 80.31; H, 8.99. Found: C, 79.96; H, 9.38.

EXAMPLE 15

5-(3-Hydroxy-3,7,11,15-Tetramethyl-6(E),10(E),14-Hexadecatrienyl)-2,3-Dimethyl-2,5-cyclohexadiene-1,4-Dione

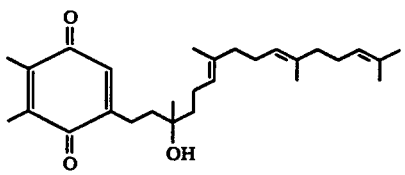

The precursor compounds were prepared by the method in Pearce, et al., *J. Med. Chem.*. 35: 3595–3606 (1992).

Orange Oil: IR (film) 3510, 2924, 1648, 1616, 1378, 1106 cm$^{-1}$; $^1$H NMR (CDCl$_3$) δ 1.23 (s, 3H), 1.50–1.70 (m, 2H), 1.59 (s, 6H), 1.62 (s, 3H), 1.67 (s, 3H), 1.9–2.10 (m, 12H), 2.00 (s, 3H), 2.02 (s, 3H), 2.50 (m, 2H), 5.09 (m, 3H), 6.52 (s, 1H); MS m/e 427 (MH+).

Anal. Calcd. for $C_{28}H_{42}O_3$: C, 78.83; H, 9.92. Found: C, 78.73; H, 10.01.

EXAMPLE 16

2-(3-Hydroxy-3,7,11,15-Tetramethyl-6(E),10(E),14-Hexadecatrienyl)-2,5-cyclohexadiene-1,4-Dione Hydrate

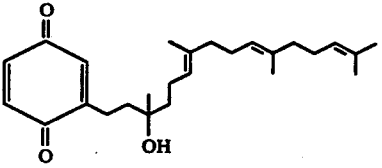

The precursor compounds were prepared by the method in Pearce, et al., *J. Med. Chem.*, 35: 3595–3606 (1992).

Orange Oil: IR (film) 3493, 2925, 1658, 1599, 1449, 1377, 1294, 1109 cm$^{-1}$; $^1$H NMR (CDCl$_3$) δ 1.23 (s, 3H), 1.50–1.65 (m, 2H), 1.59 (s, 6H), 1.62 (s, 3H), 1.66 (s, 3H), 1.9–2.10 (m, 12H), 2.50 (m, 2H), 5.11 (m, 3H), 6.58 (s, 1H), 6.68–6.77 (m, 2H); MS [FAB] m/e 421 (M+Na+).

Anal. Calcd. for $C_{26}H_{38}O_3 \cdot 0.2\ H_2O$: C, 77.63; H, 9.63; 0.91% $H_2O$. Found: C, 77.63; H, 9.58; 0.34% $H_2O$.

Other embodiments of the invention will be apparent to the skilled in the art from a consideration of this specification or practice of the invention disclosed herein. It is intended that the specification and examples be considered as examplary only, with the true scope and spirit of the invention being indicated by the following claims.

I claim:

1. A compound of the formula

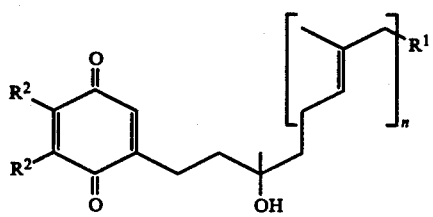

wherein
$R^1$ is H or

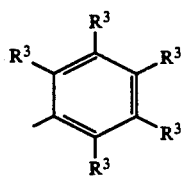

$R^2$ is $C_1$–$C_5$ alkyl, $CF_3$, CN or halogen, $R^3$ is H, $C_1$–$C_5$ alkyl, $CF_3$, CN or halogen, and n is an integer of 1 to 3, or a pharmaceutical acceptable salt, hydrate or solvate thereof.

2. The compound of claim 1 which is 5-(3-hydroxy-3,7,11,15-tetramethyl-6(E),10(E),14-hexadecatrienyl)-2,3-dimethyl-2,5-cyclohexadiene-1,4-dione.

3. The compound of claim 1 which is 2-(3-hydroxy-3,7,11,15-tetramethyl-6(E),10(E),14-hexadecatrienyl)-2,5-cyclohexadiene-1,4-dione hydrate.

4. The compound which is 2-(3-hydroxy-3,7,11,15-tetramethyl-6(E),10(E),14-hexadecatrienyl)-1,4-naphthalene-1,4-dione.

5. The compound of claim 1 which is 5-(3-hydroxy-7,11,15-trimethyl-6(E),10(E),14-hexadecatrienyl)-2,3-dimethyl-2,5-cyclohexadiene-1,4-dione.

6. The compound of claim 1 which is 2-(3-hydroxy-7,11,15-trimethyl-6(E),10(E),14-hexadecatrienyl)-2,5-cyclohexadiene-1,4-dione.

7. The compound of claim 1 which is 5-(3,7-dimethyl-3-hydroxy-9-[3-(trifluoromethyl)phenyl]-6(E)-nonenyl)-2,3-dimethyl-2,5-cyclohexadiene-1,4-dione.

8. The compound which is 2-(3,7,11-trimethyl-2(E),-6(E),10-dodecatrienyl)-2,5-cyclohexadiene-1,4-dione.

9. A pharmaceutical composition which comprises a compound of claim 1 and a pharmaceutical acceptable carrier.

10. A method of inhibiting cholesterol biosynthesis and lowering LDL cholesterol which comprises administering to an animal in need thereof an effective amount of a compound of claim 1.

11. The intermediate 2-(3,7,11-trimethyl-2(E),-6(E),10-dodecatrienyl)-1,4-hydroquinone bis-diethylcarbamate.

* * * * *